US008034288B2

United States Patent
Burns et al.

(10) Patent No.: US 8,034,288 B2
(45) Date of Patent: Oct. 11, 2011

(54) METHOD AND APPARATUS FOR CLEANING OF VIABLE DONOR SOFT TISSUE

(75) Inventors: David C. Burns, Ithaca, NY (US); Anthony R. Eisenhut, Lansing, NY (US); Renee Christopher, Dryden, NY (US); Tim W. Christensen, Greenville, NC (US)

(73) Assignee: Novasterilis, Lansing, NY (US)

( * ) Notice: Subject to any disclaimer, the term of this patent is extended or adjusted under 35 U.S.C. 154(b) by 390 days.

(21) Appl. No.: 12/019,047

(22) Filed: Jan. 24, 2008

(65) Prior Publication Data

US 2008/0166266 A1    Jul. 10, 2008

Related U.S. Application Data

(63) Continuation-in-part of application No. 11/515,926, filed on Sep. 6, 2006, now abandoned, which is a continuation of application No. 10/869,052, filed on Jun. 17, 2004, now Pat. No. 7,108,832.

(60) Provisional application No. 60/480,410, filed on Jun. 23, 2003.

(51) Int. Cl.
*A61L 2/20* (2006.01)
*A01N 1/02* (2006.01)

(52) U.S. Cl. .......................................... 422/33; 435/1.1
(58) Field of Classification Search ............... 422/33; 435/1.1
See application file for complete search history.

(56) References Cited

U.S. PATENT DOCUMENTS

| | | | |
|---|---|---|---|
| 4,681,839 A * | 7/1987 | Swartz | 435/1.1 |
| 4,944,837 A | 7/1990 | Nishikawa et al. | |
| 5,213,619 A | 5/1993 | Jackson et al. | |
| 5,370,740 A | 12/1994 | Chao et al. | |
| 5,422,377 A | 6/1995 | Aubert | |
| 5,725,579 A * | 3/1998 | Fages et al. | 128/898 |
| 5,851,483 A | 12/1998 | Nicolle et al. | |
| 5,996,155 A | 12/1999 | Chao et al. | |
| 6,149,864 A | 11/2000 | Dillow et al. | |
| 6,506,213 B1 | 1/2003 | Mandel et al. | |
| 6,518,307 B2 | 2/2003 | McKenzie et al. | |
| 6,613,278 B1 | 9/2003 | Mills et al. | |
| 6,620,356 B1 | 9/2003 | Wong et al. | |
| 6,716,457 B1 | 4/2004 | Eagles et al. | |
| 7,033,813 B2 | 4/2006 | Castor et al. | |
| 7,108,832 B2 | 9/2006 | Christensen et al. | |
| 7,160,492 B2 | 1/2007 | King | |

(Continued)

FOREIGN PATENT DOCUMENTS

EP        1782839        11/2005

OTHER PUBLICATIONS

Akkus et al., "Fracture Resistance of Gamma Radiation Sterilized Cortical Bone Allografts", Journal of Orthopaedic Research, 2001, 19: 927-934.

(Continued)

*Primary Examiner* — Sean E Conley
*Assistant Examiner* — Kevin Joyner
(74) *Attorney, Agent, or Firm* — Welsh Flaxman & Gitler LLC

(57) ABSTRACT

A process for cleaning donor soft tissue by removing contaminants by extraction using a fluid at supercritical temperature and pressures while preserving the integrity of the tissue.

8 Claims, 1 Drawing Sheet

U.S. PATENT DOCUMENTS

| 7,560,113 | B2 | 7/2009 | Christensen |
| 2003/0027125 | A1* | 2/2003 | Mills et al. ................. 435/1.1 |
| 2003/0072677 | A1 | 4/2003 | Kafesjian et al. |
| 2003/0120852 | A1 | 6/2003 | McConnell et al. |
| 2004/0033269 | A1 | 2/2004 | Hei et al. |
| 2010/0080790 | A1 | 4/2010 | Matthews et al. |

OTHER PUBLICATIONS

Cornu et al., "Effect of Freeze-Drying and Gamma Irradiation on the Mechanical Properties of Human Cancellous Bone", Journal of Orthopaedic Research, 2000, 18(3): 426-431.

Duffy et al., "An Epidemic of Corneal Destruction Caused by Plasma Gas Sterilization", Arch. Ophthalmol., Sep. 2000, 118: 1167-1176.

Godette et al., "Biomechanical Effects of Gamma Irradiation on Fresh Frozen Allografts in Vivo", Orthopedics, Aug. 1996, 19(8): 649-653.

Holyoak et al., "Toxic Effects of Ethylene Oxide Residues on Bovine Embryos in Vitro", Toxicology, 1996, 108: 33-38.

Ikarashi et al., "Cytotoxicity of Medical Materials Sterilized with Vapour-Phase Hydrogen Peroxide", Biomaterials, 1995, 16(3): 177-183.

Jahan et al., "Long-Term Effects of Gamma-Sterilization on Degradation of Implant Materials", Appl. Radiat. Isot., 1995, 46(6/7): 637-638.

Kamihira et al., "Sterilization of Microorganisms with Supercritical Carbon Dioxide", Agric. Biol. Chem., 1987, 51(2): 407-412.

Lin et al., "Inactivation of *Saccharomyces cerevisiae* by Supercritical and Subcritical Carbon Dioxide", Biotechnol. Prog., 1992, 8: 458-461.

Schiewe et al., "Toxicity Potential of Absorbed-Retained Ethylene Oxide Residues in Culture Dishes on Embryo Development in Vitro", Jour. Animal Science, 1985, 60(6):1610-18.

Spilimbergo et al., "Microbial Inactivation by High-Pressure", Journal of Supercritical Fluids, 2002, 22: 55-63.

Windebank et al., "Residual Ethylene Oxide in Hollow Fiber Hemodialysis Units is Neurotoxic in Vitro", Annals of Neurology, Jul. 1989, 26(1): 63-68.

* cited by examiner

US 8,034,288 B2

METHOD AND APPARATUS FOR CLEANING OF VIABLE DONOR SOFT TISSUE

CROSS REFERENCE TO RELATED APPLICATIONS

This application is a continuation in part of U.S. patent application Ser. No. 11/515,926, entitled "STERILIZATION METHODS AND APPARATUS WHICH EMPLOY ADDITIVE-CONTAINING SUPERCRITICAL CARBON DIOXIDE STERILANT", filed Sep. 6, 2006, which is now abandoned, which is a continuation of U.S. patent application Ser. No. 10/869,052, entitled "STERILIZATION METHODS AND APPARATUS WHICH EMPLOY ADDITIVE-CONTAINING SUPERCRITICAL CARBON DIOXIDE STERILANT", filed Jun. 17, 2004, which is now U.S. Pat. No. 7,108,832, which claims the benefit of U.S. Provisional Application Ser. No. 60/480,410, entitled "STERILIZATION METHODS AND APPARATUS WHICH EMPLOY ADDITIVE-CONTAINING SUPERCRITICAL CARBON DIOXIDE STERILANT", filed Jun. 23, 2003.

FIELD OF THE INVENTION

The present invention relates generally to the process of cleaning human, animal and in vitro-produced soft tissue and an apparatus in which a supercritical fluid such as carbon dioxide is employed as a penetrating fluid used to extract antigenic matter that can cause an inflammatory response in recipients. After the cleaning occurs the soft tissue is repackaged and then sterilized.

BACKGROUND OF THE INVENTION

The commercial viability of allograft tissues is in part a function of the physical appearance, the biocompatibility, and the mechanical properties of the tissue. Individuals responsible for the decision to use or not use a given allograft often evaluate the aesthetics of the product in reaching a decision. For example, ligament allograft material that is "yellow" is often rejected by the surgeon for implantation in favor of an allograft that is not discolored. Likewise for soft tissue, in particular, dermis and cardiovascular tissue, color and appearance are deciding factors used by most surgeons in the operating room.

Tissue banks responsible for the processing of allografts employ many different cleaning, rinsing, soaking, and washing steps in an effort to produce a product that is safe, viable for implantation, and commercially desirable. While many of the steps used meet these goals, they often fall short of effectively producing a commercially desirable and functional product. This shortcoming can stem from inadequacy of the existing process to clean the product or it may stem from damage caused by the cleaning treatment that negatively impacts the biological and biomechanical properties of the allograft.

Additionally, the numerous steps required to achieve an acceptable product for distribution add to the cost of the final graft. These steps require extra processing time and personnel, and can often vary in effectiveness. Ideally a process for preparing allografts would include a step that could preserve the essential properties of the allograft, remove the antigenic matter and any discoloration from the allograft, take a minimum amount of processing time, prepare the allograft for sterilization and increase the commercial desirability by positively impacting the aesthetics of the product.

Generally, soft tissue grafts are manually cleaned to purify them of all materials that adversely affect their implantation. Currently, most prior art techniques are found to impair both the biomechanical properties and inductive properties of the soft tissue. The prior techniques used for extraction of impurities disrupt the collagen network of the soft tissue by cross-linking or degradation, further affecting the mechanical properties of the soft tissue graft. Since, the implanting of soft tissue grafts is generally carried out for the purpose of repairing damaged soft tissue or replacing an impaired soft tissue, it is desirable to eliminate the problem of recolonization because of reduced or minimal blood flow, which is essential. It would therefore be advantageous to have available soft tissue grafts with biomechanical properties that are almost equivalent to those of natural soft tissue.

There are inherent risks involved with allografts since soft tissue is being taken from a donor generally with an unknown medical history. For example, an infectious disease from the donor could be passed on to the recipient. Apart from the risks of infection, the main complications related to the use of allografts are rejection, inflammatory response from residual foreign material in the transplanted graft and, when appropriate, the unsuccessful recolonization of the implanted soft tissue. The unsuccessful recolonization of the grafts today poses a particularly significant problem.

To mitigate these risks, various attempts aiming to reduce or eliminate these complications have been made. These procedures are generally based on the principle of extracting the blood or blood constituents and lipids from the soft tissue before implantation. Such residual blood or blood constituents and lipids contained in the soft tissue are the cause of significant rejection reactions. These rejection reactions are also related to the presence of contaminants such as endotoxins in the tissue.

The use of organic solvents to extract blood, blood constituents and lipids from soft tissue is known. The most commonly used solvents are ethylene diamine, hydrogen peroxide, ethanol, acetone and various chlorinated solvents such as chloroform or dichloromethane. However, the solvents used for protein extraction are often highly toxic. Because of this toxicity, the soft tissues must be carefully rinsed, which often proves to be difficult, given their density and delicate structure (collagenous network).

In accordance with the need for proper preparation of donor soft tissue, gentle and reliable sterilization methods are needed that result in greater than $10^6$ log reductions of microbial contaminants without impacting the properties of the donor soft tissue being sterilized.

A need has developed for sterilization of biological tissues, including macromolecular biopolymers, due to the common practice of tissue implantation. However, most sterilization techniques for soft tissue have been found to be incompatible with the tissue. Steam and gamma radiation result in a significant decrease in tissue integrity and soft tissue strength due to cross-linking. Cross-linking disrupts the collagenous network, increasing the stiffness of the collagen fibers and decreasing the mobility of the graft. Certain antibacterial washes have been used to disinfect tissue, but incomplete sterilization is achieved and the washes leave residual toxic contaminants in the tissues. Ethylene oxide also reacts with biological tissue and is thus an undesirable sterilant for such reason.

Recently, in U.S. Pat. No. 7,108,832, incorporated herein by reference and commonly owned by assignee of this application, a highly effective sterilization process is disclosed.

It therefore would be highly desirable to provide a process for cleaning soft tissue prior to the tissue being sterilized.

SUMMARY OF THE INVENTION

The present invention relates to a process for cleaning donor soft tissue to preserve the integrity of the soft tissue. First, a donor soft tissue is obtained and the topical contaminants are mechanically removed from the surface of the soft tissue. The soft tissue and an absorbent material are placed into a gas permeable package and the package sealed. The sealed package is then introduced into a reactor pressure vessel and supercritical fluid is introduced into the pressure vessel. Contact between the supercritical fluid and the soft tissue in the package is maintained while mechanically agitating the fluid for a time sufficient to solubilize contaminants contained in the soft tissue and separate the contaminants from the soft tissue by absorption into the absorbent material. The package is removed from the pressure vessel, and the tissue separated from the absorbent material in the package, thereafter the soft tissue is rinsed with a sterile solution.

The supercritical fluid used is carbon dioxide and it is introduced and removed from the pressure vessel at a rate of from about 0.01 to 5 psi/second.

It is an object of the present invention to provide an implantable biomaterial whose mechanical properties, particularly tensile strength, are at least equivalent to those of natural soft tissue.

It is an object of the present invention to provide an implantable tissue part that is free from infection and safe with respect to use with the immune system of a donee.

It is a further object of the present invention to provide an implantable soft tissue that is cosmetically and visually acceptable to surgeons.

Other objects and advantages of the present invention will become apparent from the following detailed description when viewed in conjunction with the accompanying drawings, which set forth certain embodiments of the invention.

BRIEF DESCRIPTION OF THE ACCOMPANYING DRAWINGS

Reference will hereinafter be made to the accompanying drawings, wherein like reference numerals throughout the various FIGURES denote like structural elements, and wherein.

DETAILED DESCRIPTION OF THE INVENTION

Figure 1:
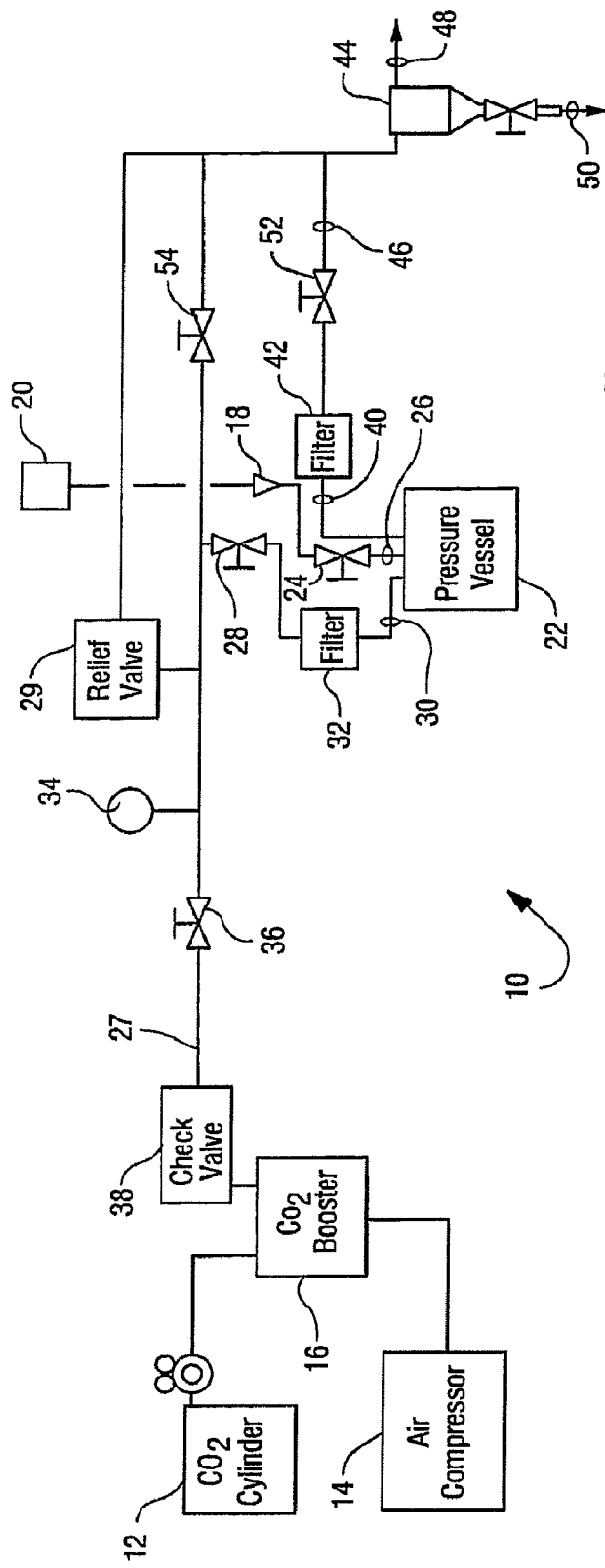
FIG. 1 is a schematic view of the cleaning/sterilizing apparatus of the present invention.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

The present invention employs a cleaning process and an apparatus used therewith using supercritical fluid such as carbon dioxide as an extractant to clean viable donor soft tissue for subsequent use such as implantation into a donee. Soft tissue as discussed in the present invention generally relates to all tissue, other than bone tissue, including but not limited to: dermis, tendons, ligaments, cardiovascular conduits, nerve tissue, heart valves, corneas, and fascia. These soft tissues contain potential contaminants of blood, blood constituents and lipidic organic matter such as fats. These potential contaminants are capable of becoming toxic, if untreated, upon implantation of the tissue into a donee human body.

The present invention provides an implantable tissue part with comparable strength to that of natural tissue that is free from infection and safe for use with the immune system of a donee, as the implant does not contain toxic products. The present invention achieves these goals while at the same time rendering those tissues acceptable in visual appearance to surgeons. The donor tissue may include thermally or hydrolytically sensitive, medically important materials, and is treated for implantation or transplantation. It is, therefore, an aim of the invention to propose an implantable biomaterial whose mechanical properties, particularly tensile strength, are at least equivalent to those of natural soft tissue. The invention also aims to propose a biomaterial that improves the efficacy of soft tissue grafts both from the mechanical and from the biological point of view.

With these goals in mind, and as will be discussed below in greater detail, the present invention concerns a process for treating animal or human tissue to obtain biomaterial which can be implanted in a human and is suitable for sustaining mechanical stresses after implantation.

According to the invention, the process for cleaning or decontaminating soft tissue having potential contaminants of blood, blood constituents and lipidic organic matter present in the tissue includes the steps of: a) cleaning the soft tissue mechanically of all the organic matter on the surface thereof, that is removing extraneous tissue, blood and fat product; b) cutting the soft tissue into a desired size and shape part; c) contacting and impregnating the soft tissue with an extractant in the form of a fluid in a supercritical state suitable for solubilizing contaminants such as blood, blood constituents and lipidic organic matter present in this tissue; d) maintaining the contact between extractant and the contaminants in the tissue for a time period sufficient to form a solute containing the contaminants in this tissue in the extractant, and e) separating the extractant containing the solute from the soft tissue thereby cleaning (i.e. removing of bio-products) the soft tissue by removing the constituents harmful to a successful re-implantation.

The soft tissue is generally first rinsed in a warm saline solution. The tissue is then mechanically cleaned prior to further processing to remove external lipids and other organic material on the surface of the soft tissue. Suitable methods of external mechanical cleaning are well known to those skilled in the art and include soft scrubbing procedures and the like.

The soft tissue is manipulated to the desired size, shape or configuration by mechanical cutting to form a tissue part. Suitable cutting means include the use of a scalpel and other means known to those skilled in the art.

Following the topical preliminary cleaning and cutting of the soft tissue specimen, the cleaning process to remove contaminants such as blood, blood constituents, minerals and lipidic organic matter potentially present in or on soft tissue is achieved in the following manner.

The soft tissue is wrapped into an absorptive material. In accordance with a preferred embodiment, the absorptive material is any medical absorbent material, such as gauze, abdominal dressing or other wound dressings. An abdominal dressing is also called a laparoscopy material, and is a material made of several layers of gauze in a rectangular shape used as a sponge for packing wounds of the viscera and abdomen. The absorbent material functions to collect the extracted material from the soft tissue as it is subsequently treated with an extractant. The wrapped soft tissue is placed into a single microporous plastic film pouch, such as Tyvek® envelopes by Dupont. The pouch must be porous to permit the passage of the supercritical fluid through the bag so as to contact the wrapped soft tissue. The pouch is then sealed and placed into a reactor pressure vessel.

The present invention utilizes a supercritical fluid to extract contaminants from the soft tissue. While numerous extractants may be used, the following description is restricted to the use of carbon dioxide for purposes of illustration only and is not limiting in the use of other supercritical fluids that are known in the art.

Figure 2:
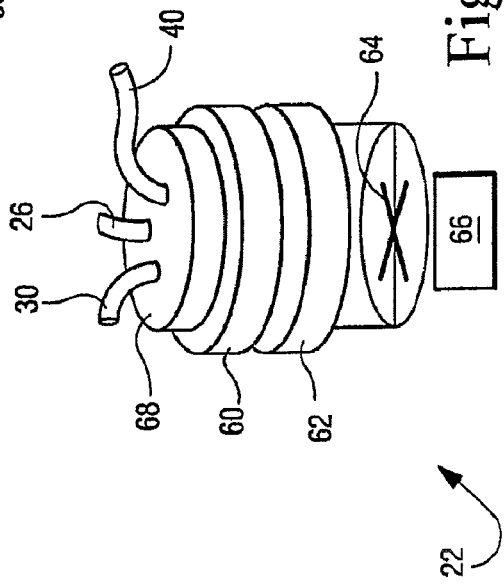
FIG. 2 is a schematic view of the reactor pressure vessel used with the present invention.

One presently preferred embodiment of an apparatus 10 according to the present invention is depicted in accompanying FIGS. 1 and 2. In this regard, it can be seen that the apparatus includes a standard compressed gas cylinder 12 containing a fluid capable of entering a supercritical state such as carbon dioxide, and a standard air compressor 14 used in operative association with a carbon dioxide booster 16 (e.g., Haskel Booster AGT 7/30). Alternatively, the air compressor 14 and carbon dioxide booster 16 can be replaced with a single carbon dioxide compressor. An additive cycle is also provided by means of an inlet port 18 which allows additive contained in reservoir 20 to be added to a reactor pressure vessel 22 through valve 24 and additive line 26. Alternatively, the additive can be introduced by soaking it into an absorbent pad and placing the pad in the reactor pressure vessel 22 with the material to be treated. The carbon dioxide is introduced to the reactor pressure vessel 22 from header line 27 via valve and regulator (herein called valve 28) and $CO_2$ supply line 30. A filter 32 (e.g., a 0.5 micron filter) is provided in the supply line 30 to prevent the escape of material from the vessel. A pressure gauge 34 is provided downstream of $CO_2$ shut-off valve 36 in supply header line 27 to allow the pressure to be visually monitored. A check valve 38 is provided in the header line 27 upstream of the $CO_2$ shut-off valve 36 to prevent reverse fluid flow into the carbon dioxide booster 16. In order to prevent an overpressure condition existing in header line 27, a pressure relief valve 9 may be provided.

An outlet line 40 through valve and regulator (herein called valve 52) allows the reactor pressure vessel 22 to be depressurized. In this regard, the depressurized fluid exits the reactor pressure vessel 22 via outline line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components.

The reactor pressure vessel 22 is most preferably constructed of stainless steel (e.g. 316 gauge stainless steel) and has a total internal volume sufficient to accommodate the materials being cleaned either on a laboratory or commercial scale. For example, in laboratory studies, an internal volume of 600 ml (e.g., approximately 8 inches long by about 2.5 inches inside diameter) was deemed adequate As is perhaps more clearly shown in FIG. 2, the reactor pressure vessel 22 includes a vibrator 60, a temperature control unit 62, and a mechanical stirring system most preferably comprised of an stirring impeller 64 and a magnetic driver 66. The reactor pressure vessel 22 contains a conventional basket (not shown) which is also preferably constructed of 316 gauge stainless steel. The basket serves to hold the wrapped soft tissue to be cleaned as well as to protect the wrapped soft tissue from the stirring impeller 64 and direct the extractant fluid in a predetermined manner.

The reactor pressure vessel 22 may be operated at a constant pressure or under continual pressurization and depressurization (pressure cycling) conditions without material losses due to splashing or turbulence, and without contamination of pressure lines via back diffusion. The valves 24, 28 and 52 allow the reactor pressure vessel 22 to be isolated and removed easily from the other components of the apparatus 10. The top 68 of the reactor pressure vessel 22 may be removed when depressurized to allow access to the vessel's interior.

In use, the wrapped soft tissue material to be cleaned is placed in a microporous pouch or package that is introduced into the basket in the interior space of the reactor pressure vessel 22 along with any initial portion of liquid additive from reservoir 20 or an additive pad. The temperature control unit 62 is operated so as to set the desired initial temperature for cleaning and sterilization. The reactor pressure vessel 22 may then be pre-equilibrated with carbon dioxide from gas cylinder 12 at atmospheric pressure, following which the magnetic driver 66 is operated so as to activate the stirring impeller 64. The reactor pressure vessel 22 may thereafter be pressurized to a desired pressure by introducing additional carbon dioxide gas from gas cylinder 12 via the air compressor 14 linked to carbon dioxide booster 16.

In order to affect a pressure cycling of the reactor pressure vessel 22, an amount of carbon dioxide may be released therefrom via depressurization outline line 40 by momentarily opening valve 52 sufficient to partially reduce pressure within the reactor pressure vessel 22. Additive may be introduced into the reactor pressure vessel 22 for any given pressure cycle by opening valve 24 which allows liquid additive to flow from reservoir 20 into inlet port 18. It will be understood that the cleaning promoter additives may be introduced prior to pressurization and/or during pressure cycling. Prior to pressurization, additives are introduced directly into the reactor pressure vessel 22 prior to sealing and/or via the additive port 18. The additives are most preferably introduced during the cycling stages by measured addition to the additive port 18 at ambient pressures. The port 18 is subsequently sealed and the additive chamber is pressurized so that the additive may enter the reactor pressure vessel 22 without altering the internal pressure. The exact mechanism of addition may be modified such that the process is more efficient and/or convenient.

Following additive introduction, the reactor pressure vessel 22 may be repressurized to a desired pressure following introduction of the liquid additive therein. Such depressurization/repressurization with introduction of liquid additive may be repeated for any number of cycles that may be desired. The cycle of depressurization and repressurization as well as the introduction of the carbon dioxide and liquid additive may be automatically controlled via a controller screen which sequences the various valves discussed previously so as to achieve the desired pressure conditions and cycles.

In the treatment of the wrapped soft tissue it has been found that it is desirable to precisely control the pressurization and depressurization rates in the sterilization vessel to maintain the physical structure and appearance of the soft tissue. For these products, the input or flow of $CO_2$ through valve 24 into the reactor pressure vessel 22 is regulated to 0.01 to 5 psi/second. Regulating the rate of pressurization is also intended to control mass flow (1000 mg/second) of $CO_2$ into the reactor pressure vessel 22. In the initial fill, the valve 24 is opened and allowed to flow at the regulated rate using the ambient pressure of the $CO_2$ supply from the gas cylinder 12. The $CO_2$ supply pressure can range from 75 psi to approximately 900 psi or greater. Once the pressure in reactor pressure vessel 22 reaches equilibrium with the $CO_2$ supply source pressure, the pumping of the $CO_2$ using the carbon dioxide booster 16 begins. The $CO_2$ booster rate of pressurization is regulated to not exceed 5 psi/second. Once the reactor pressure vessel 22 reaches its operating pressure of 1500 psi, the process is allowed to continue through its normal path. Upon completion of the desired time period at the operating temperature and pressure, depressurization of the reactor pressure vessel 22 then occurs. At this point the output valve 52 is opened enough that the rate of depressurization is regulated to less than 5 psi/second. Regulating the rate of depressurization is also intended to control of mass flow of $CO_2$ out of the reactor pressure vessel 22. The rate of depressurization is controlled at this rate until the ambient pressure in the reactor pressure vessel 22 is zero or at equilibrium with the atmospheric pressure. Ambient conditions are generally zero psi and 25° C. The pressurization and depressurization rates discussed above where found to be critical, that is no damage resulted to the collagenous network of the tissue being cleaned when these rates were employed.

Most preferably, periodic agitation to the contents of reactor pressure vessel 22 is effected using a vibrator 60 through the entire process. Intermittent or continuous agitation of the reactor pressure vessel 22 and its contents is performed by vibrating the reactor pressure vessel 22 during cleaning. Agitation enhances mass transfer of the carbon dioxide and additives by eliminating voids in the fluid such that the material being cleaned comes into more complete contact with extractant. The specific means of agitation may be adjusted to accommodate the particular apparatus employed and to optimize sterilization times, temperatures, and pressure cycles. When cleaning is complete, the reactor pressure vessel 22 is depressurized, the magnetic driver 66 is stopped thereby stopping the stirring impeller 64, and the package or pouch containing wrapped soft tissue is removed by opening top 68 of reactor pressure vessel 22.

Upon run completion, each tissue sample is removed from its pouch, unwrapped from the absorbent material, which is generally filled with blood and blood constituents, and other extracted residuals, and rinsed in a sterile fluid such as saline to remove any blood or constituent residuals on surface. The tissue samples are then packaged under sterilization conditions.

The extractant that is used to clean and penetrate the soft tissue is a fluid in a supercritical state suitable for cleaning (i.e. killing of microbial contaminants) the soft tissue. The fluid in the supercritical state is caused to penetrate throughout the soft tissue thereby cleaning by extraction the potential contaminants on the surface or within the tissue.

According to the invention, the fluid in the supercritical state penetrates the soft tissue that is potentially contaminated with blood, blood constituents and/or lipidic organic matter present in the tissue. These contaminants are solubilized in the fluid, extracted and separated from the soft tissue. The extraction thus effected by this supercritical fluid has properties particularly suitable to the treatment and sterilization of the soft tissue without having a deleterious effect of the physical properties of the tissue.

More particularly, this extraction is beneficial for the following reasons. Under normal conditions blood supplies oxygen and nutrients while removing waste products from tissue. Any residual blood in the allograft likely contains metabolic waste and ions from the donor and can cause inflammation if left in the allograft. In addition, blood plasma contains 90% water, 7-8% proteins (albumin, fibrinogen, plasminogen, thrombin, basically the clotting proteins), 1% electrolytes (NaCL, K+, Ca2+) and 1% substances in transit (hormones, urea, lipids, vitamins, amino acids and glucose). On the surface of red blood cells are various substances, among which 29 different compounds have been identified, including the antigens and Rh factor. If a patient is exposed to blood group antigens or foreign material not recognized by its immune system, such exposure triggers an immune response leading to a potentially life-threatening inflammatory response.

The cleaning process of the present invention is practiced using an extractant such as carbon dioxide at pressures between about 1000 to about 3500 psi, at temperatures in the range between about 25° C. to about 60° C. Most preferably, the donor tissue to be cleaned is subjected to carbon dioxide at or near such pressure and temperature conditions for times ranging from about 1 minutes to about 12 hours. The carbon dioxide employed in the practice of the present invention is most preferably substantially pure. Thus, trace amounts of other gases may be tolerated provided that the cleaning or extracting properties of the carbon dioxide are not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

To determine the amount of blood and blood constituents and "other material" extracted, pre and post process weight of the tissue are taken and recorded. The extraction/cleaning process is run multiple times to ensure that no additional material is extracted. Although, this may take multiple runs, the amount of extracted material significantly decreases on each run.

This process of placing the tissue part and absorbent material in a gas permeable package permits removal of organics and microbial contamination without creating cross donor issues as the contaminates do not escape from the individual packages being simultaneously processed.

More specifically, the preferred process of cleaning the soft tissue occurs by the following process.

The soft tissue is rinsed in a warm saline solution. The saline solution includes approximately 9 grams of salt per liter and has a pH of between 7.2 and 7.4 and maintained at a temperature of above room temperature up to around 40° C. The tissue is then mechanically cleaned prior to further processing to remove external lipids and other organic material on the surface of the soft tissue.

The soft tissue is manipulated to the desired size, shape or configuration by mechanical cutting to form a tissue part, which is then placed into a wide mouth screw top container and rinsed in the saline solution 4 to 8 times while the container is constantly agitated. Each rinse last about 5 minutes and between rinses the soft tissue part is blotted with an absorptive material to remove excess saline solution and residual materials on the tissue surface.

Thereafter, the tissue part is packaged in a single gas permeable sleeve or pack, such as Steripack®, wrapped in or along with an absorptive pad loaded with 16 ml of the warm saline solution. The sleeve or pack is sealed and placed into a basket. The basket is then loaded into a reactor vessel.

The reactor vessel generally holds three stacked baskets and it is preferred to place the packages in the middle basket leaving the top and bottom baskets empty. The lid on the vessel is closed and operation begins upon activation of the start button.

The reactor vessel is programmed to run 20 minutes at the standard parameters, that are 1436 psi, 700 rpm, 33° C. The 700 rpm is the speed at which the basket is agitated during processing. Once the reactor vessel activated and the following occurs 1) Pressurization to supercritical in 5-15 minutes; 2) Process runs for 20 minutes at the above parameters; and then 3) Depressurization within in 12-25 minutes to 0 psi After depressurization the lid is opened, the baskets are removed, the package from middle basket is retrieved and once again the tissue part is rinsed with the warm saline solution in a container while being agitated for 5 minutes and then blotted dry to remove excess saline solution.

If desired or needed the tissue part is repackaged into a new sleeve with an absorbent pad and the process in the reactor vessel repeated until there is no extracted material visible in the absorptive pad.

Once processing in the vessel is completed the package is removed and the tissue part is put into a container and rinsed with 495 mls the warm saline solution plus 5 mls TX-100 (surfactant solution). The container filled with the solution is then placed on a shaking water bath for 30 minutes, which runs at 325 rpm and 40° C. The shaking water bath made be any well known device such as the SBS30 by Equilabs Canada Inc.

The solution in the container is then emptied and the tissue part rinsed again with the saline solution 1-4 times while the container is constantly agitated. Each rinse last about 5 minutes and between rinses the soft tissue part is blotted with an absorptive material to remove excess saline solution and residual materials on the tissue surface.

The solution in the container is then emptied and the tissue part is put into a container back in the container and rinsed with a solution comprising water and 3% $H_2O_2$ that is a 30 ml of 50% $H_2O_2$ and 470 ml of water solution. The container filled with the solution is then placed on a shaking water bath for 30 minutes, which runs at 325 rpm and 40° C.

The solution in the container is then emptied and the tissue part rinsed again with the saline solution 1-3 times while the container is constantly agitated. Each rinse last about 5 minutes and between rinses the soft tissue part is blotted with an absorptive material to remove excess saline solution and residual materials on the tissue surface.

The solution in the container is then emptied and the tissue part is put into a container back in the container and rinsed with a solution comprising water and 70% isopropanol. The container filled with the solution is then placed on a shaking water bath for 30 minutes, which runs at 550 rpm and 40° C.

The solution in the container is then emptied and the tissue part rinsed again with the saline solution 1-3 times while the container is constantly agitated. Each rinse last about 5 minutes and between rinses the soft tissue part is blotted with an absorptive material to remove excess saline solution and residual materials on the tissue surface.

The solution in the container is then emptied and the tissue part rinsed with deionized water 1-2 times while the container is constantly agitated. Each rinse last about one minute and then the tissue part is removed and blotted with a paper towel.

Utilization of this cleaning process improves the resulting graft product, resulting in a better healing process for the recipient of the tissue. In particular, for transplanted soft tissue, skin, etc there are several stages of healing and the present cleaning process improves the graft product resulting in a better healing process. The healing phases include:

Inflammatory phase—The blood in the region (blood cells), platelets predominantly secrete factors (growth factors, fibrin) and other extracellular matrix molecules that lay a temporary "bed" in the area of transplant (around the edges). The fact that donor blood is not present in the graft allows the host's system to begin the healing process as opposed to the rejection/inflammatory response. If there is an inflammatory response, the host will produce cells that attack the unknown blood product or material in the region, causing swelling, redness, immobility and possibly destruction of the graft.

The provisional matrix (allograft and the host cells surrounding the graft) then allows endothelial cells and fibroblasts to begin moving in and binding in the region. The cleaning process not only removes inhibitory elements but it also creates a more open structure allowing for more consistent penetration of host factors.

Proliferative phase—will secrete more extracellular matrix proteins (fibronectin, collagen) adding and building the matrix. The local cells (macrophages, endothelial cells) continually remodel the matrix.

Repopulation of host cells—The cells are proliferating during this time. Capillaries are formed from the endothelial cells (revascularization).

Maturation phase—this is where the cells continue to remodel the collagen and in where the scar is formed.

The present cleaning process reduces the required time down to 1 hour from the 20 hours commonly required in conjunction with previously available cleaning processes. In addition, the present cleaning process has lower exposure time to harmful chemicals and therefore minimizes the amount of collagen crosslinking, which maintains important physical properties such as elasticity.

Sterilization

In accordance with a preferred embodiment, once the cleaning is complete and the appropriate amount of biomaterials are removed sterilization is accomplished by the process set forth in commonly owned U.S. Pat. No. 7,108,832 which incorporated herein by reference.

The invention claimed is:

1. A process for cleaning donor soft tissue to preserve the integrity of the soft tissue comprising:
    obtaining a donor soft tissue;
    mechanically removing external lipids and other organic material on the surface of the soft tissue;
    cutting the soft tissue into the desired size and shape to form a tissue part;
    placing tissue part and an absorbent material into a gas permeable package and sealing the package;
    placing the package into a reactor pressure vessel;
    introducing supercritical carbon dioxide fluid to the pressure vessel;
    maintaining the tissue part in contact with the fluid while mechanically agitating the fluid for a time sufficient to impregnate the tissue part with carbon dioxide and to extract excessive organic matter from the tissue part; and
    removing the tissue part from the package and separating from the absorbent material and rinsing the tissue part with a sterile solution.

2. The process for cleaning donor soft tissue of claim 1 wherein the supercritical carbon dioxide fluid is introduced and removed from the pressure vessel at a rate of from about 0.01 to 5 psi/second.

3. A process for cleaning donor soft tissue to preserve the integrity of the soft tissue comprising:
    obtaining a donor soft tissue;
    mechanically removing topical contaminants from the surface of the soft tissue;
    placing the soft tissue and an absorbent material into a gas permeable package and sealing the package;
    placing the package into a reactor pressure vessel;
    introducing supercritical fluid into the pressure vessel;
    maintaining contact between the supercritical fluid and the soft tissue in the package while mechanically agitating the fluid for a time sufficient to solubilize contaminants contained in the soft tissue and separate the contaminants from the soft tissue by absorption into the absorbent material; and removing the package from the pressure vessel, separating the tissue from the absorbent material in the package and rinsing the tissue with a sterile solution.

4. The process for cleaning donor soft tissue of claim 3 wherein the supercritical fluid is introduced and removed from the pressure vessel at a rate of from about 0.01 to 5 psi/second.

5. The process for cleaning donor soft tissue of claim 3 wherein the supercritical fluid used is carbon dioxide.

6. A process for cleaning donor soft tissue to preserve the integrity of the soft tissue comprising:
   obtaining a donor soft tissue;
   placing the soft tissue and an absorbent material into a gas permeable package and sealing the package;
   placing the package into a reactor pressure vessel;
   introducing a supercritical extractant fluid capable of extracting excessive organic matter from the soft tissue into the pressure vessel;
   maintaining contact between the supercritical extractant fluid and soft tissue for a time sufficient to impregnate the soft tissue with the supercritical extractant fluid and extracting excessive organic matter from the soft tissue; and
   recovering the soft tissue from the package and separating the soft tissue from the absorbent material in the package.

7. The process for cleaning donor soft tissue of claim 6 wherein the supercritical fluid is introduced and removed from the pressure vessel at a rate of from about 0.01 to 5 psi/second.

8. The process for cleaning donor soft tissue of claim 6 wherein the supercritical fluid used is carbon dioxide.

* * * * *